United States Patent
Jung et al.

(10) Patent No.: US 9,897,583 B2
(45) Date of Patent: Feb. 20, 2018

(54) APPARATUS AND METHOD FOR DETECTING FILTER CONTAMINATION OF A FUEL CELL

(71) Applicant: Hyundai Motor Company, Seoul (KR)

(72) Inventors: Myung Ju Jung, Daejeon (KR); Hyuck Roul Kwon, Gyeonggi-do (KR); Sang Hoon Seo, Gyeonggi-do (KR); Jeong Hee Park, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 14/790,021

(22) Filed: Jul. 2, 2015

(65) Prior Publication Data
US 2016/0161457 A1    Jun. 9, 2016

(30) Foreign Application Priority Data
Dec. 9, 2014    (KR) .................... 10-2014-0176051

(51) Int. Cl.
| G01N 33/00 | (2006.01) |
| G01N 27/04 | (2006.01) |
| H01M 8/0662 | (2016.01) |
| H01M 8/04664 | (2016.01) |

(52) U.S. Cl.
CPC .... *G01N 33/0036* (2013.01); *H01M 8/04686* (2013.01); *H01M 8/0687* (2013.01); *G01N 27/04* (2013.01); *G01N 27/046* (2013.01); *H01M 8/0675* (2013.01); *H01M 2250/20* (2013.01); *Y02T 90/32* (2013.01)

(58) Field of Classification Search
CPC ............ H01L 27/2436; G11C 2213/79; Y10S 257/904; G01N 27/04; G01N 33/0036; H01M 8/04313
USPC .............. 257/249, 529, 904; 422/98; 436/60
See application file for complete search history.

(56) References Cited

U.S. PATENT DOCUMENTS

| 5,369,979 | A | * | 12/1994 | Aylsworth | ........... G01N 29/024 |
| | | | | | 73/24.01 |
| 2002/0149380 | A1 | | 10/2002 | Sato et al. | |
| 2002/0157359 | A1 | | 10/2002 | Stenersen et al. | |
| 2005/0076623 | A1 | | 4/2005 | Stenersen et al. | |
| 2005/0189223 | A1 | * | 9/2005 | Yamaguchi | .......... G01N 27/125 |
| | | | | | 204/431 |
| 2006/0292426 | A1 | | 12/2006 | Stenersen et al. | |
| 2012/0194146 | A1 | * | 8/2012 | Longacre | ................ G06F 1/266 |
| | | | | | 323/234 |

(Continued)

FOREIGN PATENT DOCUMENTS

| JP | 2006-0343282 A | 12/2006 |
| KR | 10-2003-0085106 A | 11/2003 |
| KR | 10-2007-0072926 A | 7/2007 |

(Continued)

*Primary Examiner* — Dennis White
*Assistant Examiner* — Bryan Kilpatrick
(74) *Attorney, Agent, or Firm* — Mintz Levin Cohn Ferris Glovsky and Popeo, P.C.; Peter F. Corless

(57) ABSTRACT

An apparatus for detecting a filter contamination of a fuel cell includes: a signal transmitter configured to transmit at least one signal; a signal receiver configured to receive the at least one signal from the signal transmitter; and a resistor unit including a silver compound disposed between the signal transmitter and the signal receiver and having a resistance which varies according to a chemical reaction.

16 Claims, 4 Drawing Sheets

(56) References Cited

U.S. PATENT DOCUMENTS

2014/0176142 A1 6/2014 Park et al.

FOREIGN PATENT DOCUMENTS

| KR | 10-2011-0062111 A | 6/2011 |
| KR | 10-2012-0058895 A | 6/2012 |
| KR | 10-2012-0086101 A | 8/2012 |
| KR | 10-2014-0081947 A | 7/2014 |

* cited by examiner

APPARATUS AND METHOD FOR DETECTING FILTER CONTAMINATION OF A FUEL CELL

CROSS-REFERENCE TO RELATED APPLICATION

This application claims priority to and the benefit of Korean Patent Application No. 10-2014-0176051, filed on Dec. 9, 2014 in the Korean Intellectual Property Office, the disclosure of which is incorporated herein in its entirety by reference.

TECHNICAL FIELD

The present disclosure relates generally to an apparatus and a method for detecting a filter contamination of a fuel cell, and more particularly, to techniques for determining whether to replace a filter by detecting a contamination of a fuel cell.

BACKGROUND

A fuel cell may replace a battery for supplying power to consumable electronic goods, such as a laptop computer, a mobile phone, a smart device, and the like, and may be finely processed to directly supply power to computer chips. Additional commercial applications of the fuel cell are possible. For example, fuel cells may replace an internal combustion engine for a vehicle.

Known configurations of the fuel cell commonly require oxygen for performing a chemical process of a battery. Other power sources such as an internal combustion engine (e.g., a diesel engine) also require oxygen. In most commercial purposes, it is preferable to directly supply the oxygen from the atmosphere.

However, pollutants are present in the atmosphere. The pollutants may include larger particles such as loose debris, worms, and tree blossom or smaller particles floating in the atmosphere, such as dust, pollen, smog, and smoke particles. Chemical pollutants are also widely present in the atmosphere. Typical chemical pollutants may include aromatic hydrocarbons, methanol, butane, propane, and other hydrocarbons and volatile organic compounds such as ammonia, nitrogen oxide, ozone, smog, sulfur oxide, carbon monoxide, and hydrogen sulfide.

Since efficient operation of the fuel cell relies on a chemical reaction in which chemicals are elaborately balanced, the pollutants in the air which are used in the battery may produce a side effect during operation of the battery, thereby potentially interrupting the operation of the fuel cell. Therefore, a fuel cell device can be designed to remove harmful pollutants and include a filtering device to filter said pollutants.

SUMMARY

The present disclosure has been made to solve the above-mentioned problems occurring in the related art while advantages achieved by the related art are maintained intact.

An aspect of the present disclosure provides an apparatus and a method for detecting a filter contamination of a fuel cell capable of determining whether to replace a chemical filter within a fuel cell contaminated by foreign materials or impurities of air such as a sulfur compound. Other objects and advantages of the present disclosure can be appreciated by the following description and will be clearly described by the embodiments of the present disclosure. Also, it can be easily understood that the objects and advantages of the present disclosure can be realized by the units and combinations thereof recited in the claims.

According to embodiments of the present disclosure, an apparatus for detecting a filter contamination of a fuel cell includes: a signal transmitter configured to transmit at least one signal; a signal receiver configured to receive the at least one signal from the signal transmitter; and a resistor unit including a silver compound disposed between the signal transmitter and the signal receiver and having a resistance which varies according to a chemical reaction.

The apparatus may further include: another resistor unit disposed between the signal transmitter and the signal receiver.

The resistor unit may be formed in a thin film form including silver.

The resistor unit may be formed in a hot film structure, a heat ray structure, or a semiconductor heater structure.

The received at least one signal may have a frequency which varies in response to a variance of the resistance of the resistor unit.

The apparatus may further include: a filter using a total harmonic distortion (THD) calculated by dividing a harmonic size of the frequency output from the signal receiver by a harmonic size of the frequency input to the signal transmitter and then multiplying the divided result by 100.

Contamination of the filter may be detected in real-time based on the calculated THD.

The filter may be contaminated when the calculated THD is greater than or equal to a predetermined THD.

The apparatus may further include: an alarm that is activated when the filter is contaminated.

Furthermore, according to embodiments of the present disclosure, a method for detecting a filter contamination of a fuel cell includes: transmitting at least one signal; passing the transmitted at least one signal through a resistor unit including a silver compound having a resistance which varies according to a chemical reaction; and receiving the at least one signal passing through the resistor unit.

The method may further include: passing the at least one signal through another resistor unit.

The resistor unit may be formed in a thin film form including silver.

The resistor unit may be formed in a hot film structure, a heat ray structure, or a semiconductor heater structure.

The received at least one signal may have a frequency which varies in response to a variance of the resistance of the resistor unit.

The method may further include: calculating a THD used by a filter by dividing a harmonic size of an outputted frequency by a harmonic size of an inputted frequency and multiplying the divided result by 100.

The method may further include: detecting contamination of the filter in real-time based on the calculated THD.

The filter may be contaminated when the calculated THD is greater than or equal to a predetermined THD.

The method may further include: activating an alarm when the filter is contaminated.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION OF THE EMBODIMENTS

The foregoing objects, features and advantages will become more apparent from the following detailed description of embodiments of the present disclosure with reference to accompanying drawings, which are set forth hereinafter. Accordingly, those having ordinary knowledge in the related art to which the present disclosure pertains will easily embody technical ideas or spirit of the present disclosure. Further, when the detailed description of technologies known in the related art are considered to make the gist of the present disclosure obscure in the present disclosure, the detailed description thereof will be omitted. Hereinafter, embodiments of the present disclosure will be described in detail with reference to the accompanying drawings.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Figure 1:
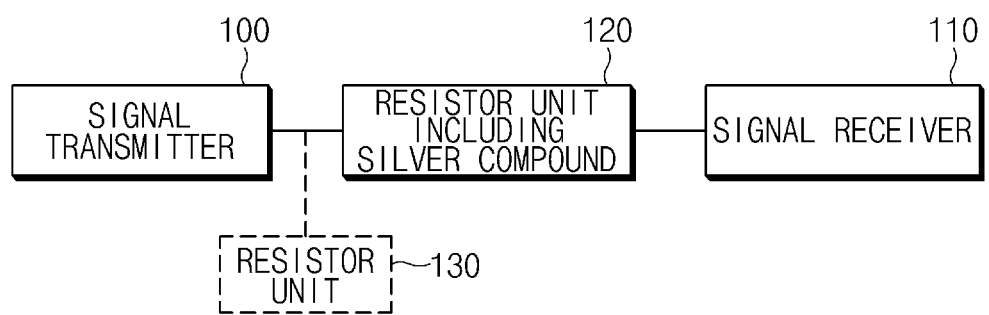
FIG. 1 is a configuration diagram for describing an apparatus for detecting a filter contamination of a fuel cell according to embodiments of the present disclosure.

Referring now to the disclosed embodiments, FIG. 1 is a configuration diagram for describing an apparatus for detecting a filter contamination of a fuel cell according to embodiments of the present disclosure.

As shown in FIG. 1, an apparatus for detecting a filter contamination of a fuel cell includes a signal transmitter 100, a signal receiver 110, and a resistor unit 120 including a silver compound.

The signal transmitter 100 transmits at least one frequency, voltage, or current to the signal receiver 110. In this configuration, the signal transmitter 100 may transmit a laser, a beam, or other signals in addition to the frequency, the voltage, or the current to the signal receiver 110.

The signal receiver 110 receives at least one the frequency, the voltage, or the current from the signal transmitter 100 and measures the received frequency, voltage, or current. The signal transmitter 100 and the signal receiver 110 may further include another resistor unit 130 in addition to the resistor unit 120 including the silver compound.

The resistor unit 120 including the silver compound has a resistance which varies by a chemical reaction, is disposed between the signal transmitter 100, and the signal receiver 110, and is configured of a resistance material to which the silver compound is added. The resistor unit 120 including the silver compound may be a thin film form including silver. Since the resistor unit 120 including the silver compound may have a resistance value which may vary due to external temperature, an error may occur during a signal processing process, and therefore a structure of correcting the external terminal using a heat generation apparatus is required. As the structure of correcting the external temperature, a hot film structure, a heat ray structure, a semiconductor heater structure, and the like may be used.

Further, the hot film structure increases a temperature of a silver thin film resistance material to make a specific C value and may change an attenuation region of a frequency based on a change in the C value. The resistor unit 120 having the silver compound does not react to air or water, but reacts to a sulfur compound or a nitrogen compound to be change from light gray to black and may detect a lifespan of the fuel cell filter using characteristics in which resistance value is changed.

Further, in the case of the general metal, when temperature increases, a resistance value of metal is increased, but when the resistor unit 120 including the silver compound is contaminated due to the sulfur compound and the nitrogen compound, even though temperature rises, the resistance value of the resistor unit 120 including the silver compound may fall. Further, the signal transmitter 100 within the apparatus for detecting a filter contamination of a fuel cell transmits an input signal and the signal receiver 110 receives the output input signal to determine a difference between a normal state and an abnormal state, thereby detecting whether a chemical filter within the fuel cell is contaminated in real time. That is, the apparatus for detecting a filter contamination of a fuel cell may measure the contamination of the chemical filter within the fuel cell using the difference between an input voltage or an input current and an output voltage or an output current which occurs while the resistance value of the resistor unit 120 including the silver compound varies due to the sulfur compound and the nitrogen compound when the signal transmitter 100 transmits the input signal.

In detail, the apparatus for detecting a filter contamination of a fuel cell may measure the contamination of the filter using a total harmonic deviation (THD) of a harmonic size of the output frequency occurring from the resistor unit 120 having the silver compound and a harmonic size of the input frequency when the signal transmitter 100 transmits the input signal and may inform a driver of the replacement of the fuel cell filter by activating an alarm when the THD of the input frequency to the output frequency is larger than the THD of the input frequency to the preset output frequency.

Figure 2:
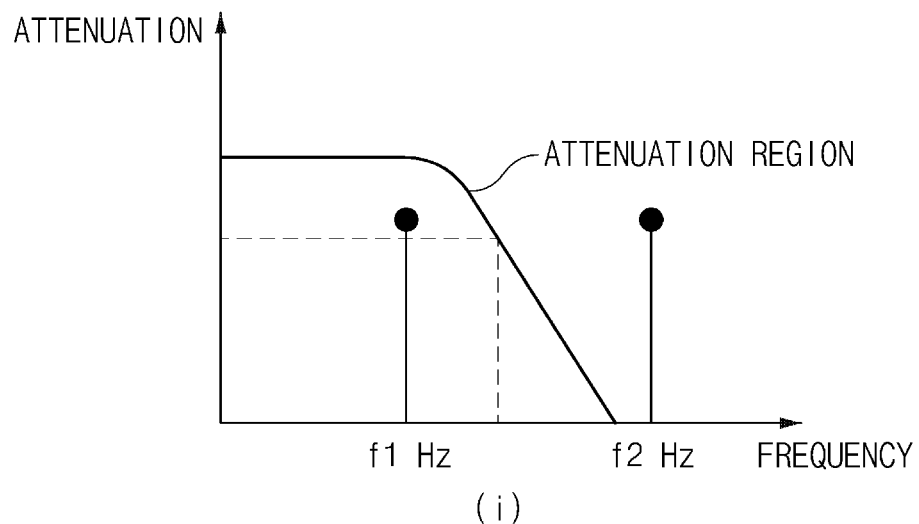
FIGS. 2I and 2II are diagrams for describing a contamination of a filter measured using the apparatus for detecting a filter contamination of a fuel cell according to embodiments of the present disclosure.
Figure 2:
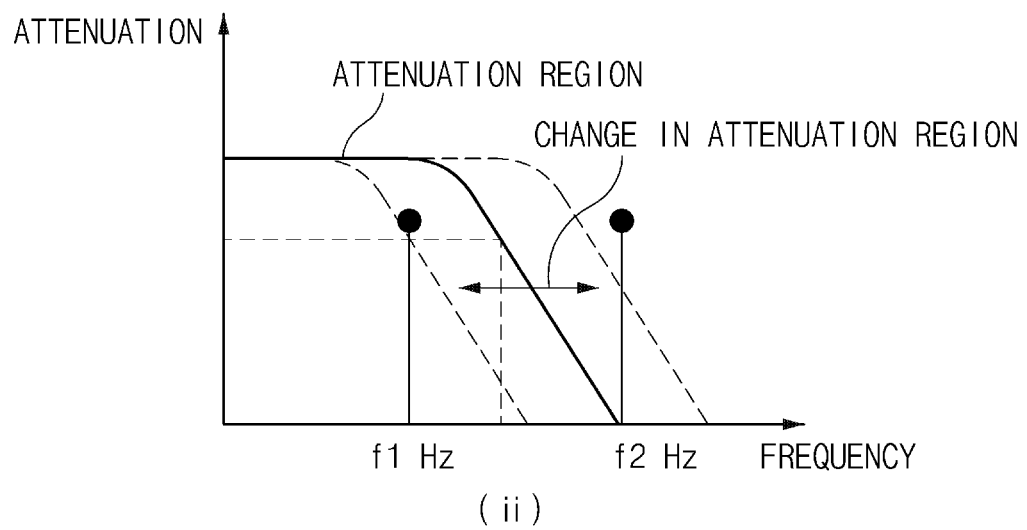

FIGS. 2I and 2II are diagrams for describing a contamination of a filter measured using the apparatus for detecting a filter contamination of a fuel cell according to embodiments of the present disclosure.

As shown in FIGS. 2I and 2II, when detecting the contamination of the filter in real-time by the frequency input, the apparatus for detecting a filter contamination of a fuel cell outputs the output signals in the normal state and the abnormal state. When the filter is contaminated due to the sulfur compound, the resistance value of the resistor unit including the silver compound varies and a signal different from the existing signal may be input or a distortion of the signal may occur. In this case, the contamination of the filter may be measured in real time by using the distortion ratio. The distortion of the signal means that the region through which the frequency passes and the region in which the frequency is attenuated vary and it may be determined whether the filter is contaminated by using the varying frequency.

The apparatus for detecting a filter contamination of a fuel cell may measure the frequency in the normal state and the frequency in the abnormal state and may measure the contamination of the filter using the total harmonic distortion (THD) of the input frequency to the output frequency. The THD represents a ratio of frequency components which is an integer multiple of a fundamental frequency. In particular, the harmonic means a physical electric amount which corresponds to an integer multiple which is 2 to 4 times as high as the fundamental frequency.

The output harmonic may be calculated using a THD method, in which the THD is a total harmonic distortion ratio and is a generation ratio of the distorted frequency when a frequency is input to a non-linear system. According to the calculation method of the THD, a value is obtained by dividing a harmonic size of the output frequency by a harmonic size of the input frequency and multiplying the divided value by 100. In the case of the normal apparatus for detecting a filter contamination of a fuel cell, no distorted frequency for the fundamental input frequency is present and therefore the THD approximates 0%. When the resistor unit including the silver compound is contaminated due to the sulfur compound or the nitrogen compound, the signal distortion for the fundamental frequency occurs and the output frequency has a value which is greater than or equal to 0%. That is, when the resistance material including the silver compound is contaminated due to the sulfur compound, the distortion of the output signal for the input signal occurs and the distortion ratio is calculated by an ECU or a signal processor and it may be diagnosed whether the failure occurs based on the calculated distortion ratio.

Figure 3:
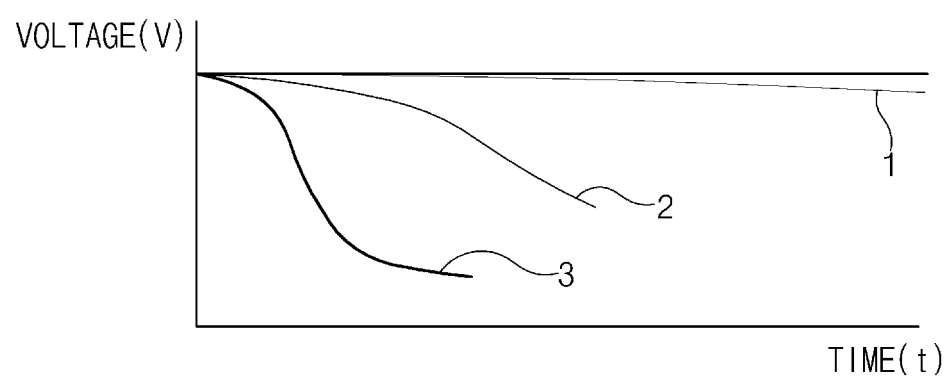
FIG. 3 is a diagram for describing a reduction in performance of the apparatus for detecting a filter contamination of a fuel cell due to a sulfur compound.

FIG. 3 is a diagram for describing a reduction in performance of the apparatus for detecting a filter contamination of a fuel cell due to a sulfur compound. FIG. 3 is a graph illustrating the reduction in the performance of the fuel cell due to the contamination by the sulfur compound including sulfur dioxide, hydrogen sulfide, or the like, in the fuel cell.

Graph 1 represents the state in which the change in voltage is insignificant over time when the resistor unit is not contaminated due to the sulfur compound. Graph 2 and graph 3 illustrate that a voltage is suddenly changed over time when the resistor unit is contaminated due to the sulfur compound (when the concentration of the sulfur compound is increased). That is, it may be appreciated that as the concentration of the sulfur compound is increased, the performance of the fuel cell is suddenly reduced.

Figure 4:
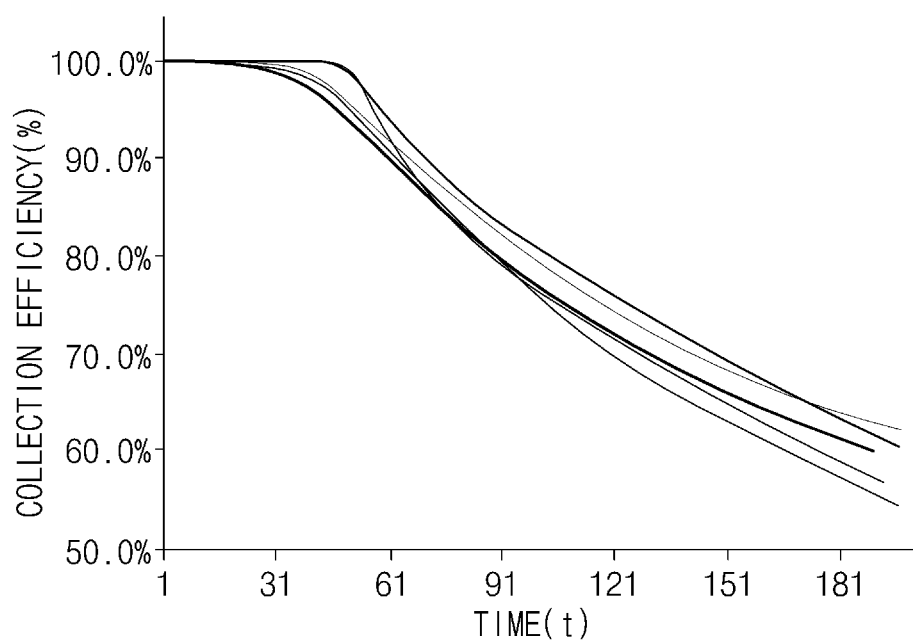
FIG. 4 is a graph illustrating a lifespan of a fuel cell filter depending on a driving distance of a vehicle.

FIG. 4 is a graph illustrating a lifespan of a fuel cell filter depending on a driving distance of a vehicle. In the case of the general dust filter, it may be determined whether the contamination occurs by predicting the lifespan of the dust filter due to the increase in the difference pressure to the initial performance, but in the case of the chemical filter, the chemical contamination is not linearly increased depending on the driving distance and therefore the replacement period of the chemical filter may not be predicted. FIG. 4 is a graph illustrating collection efficiency for the vehicles having different driving distances which are each distributed differently.

In this regard, the chemical filter of the fuel cell is vulnerable to the contamination by the sulfur compound or the nitrogen compound, but there is no large difference in the lifespan of the chemical filter of the fuel cell depending on the driving distance of the vehicle.

As described above, according to embodiments of the present disclosure, it is possible to confirm filter contamination of the fuel cell in real-time while the vehicle is being driven. Further, it is possible to improve the durability of the fuel cell by immediately replacing the fuel cell contaminated filter.

Although embodiments of the present disclosure have been disclosed based on restricted configuration and drawings, the technical ideas of the present disclosure are not limited thereto. Therefore, those skilled in the art will appreciate that various modifications and changes may be made, without departing from the scope and spirit of the present disclosure as disclosed in the accompanying claims.

What is claimed is:

1. An apparatus for detecting a filter contamination of a fuel cell, comprising:
   a signal transmitter configured to transmit at least one signal;
   a signal receiver configured to receive the at least one signal from the signal transmitter; and
   a resistor unit including a silver compound disposed between the signal transmitter and the signal receiver and having a resistance value which varies according to a chemical reaction and determining whether contamination by sulfur occurs when the resistance value falls, and
   an electronic control unit (ECU) configured to determine the contamination of a filter using a total harmonic distortion (THD) calculated by dividing a harmonic size of a frequency output from the signal receiver by a harmonic size of a frequency input to the signal transmitter and multiplying the divided result by 100.

2. The apparatus according to claim 1, further comprising:
   another resistor unit disposed between the signal transmitter and the signal receiver.

3. The apparatus according to claim 1, wherein the resistor unit is formed in a thin film form including silver.

4. The apparatus according to claim 1, wherein the resistor unit is formed in a hot film structure, a heat ray structure, or a semiconductor heater structure.

5. The apparatus according to claim 1, wherein the received at least one signal has a frequency which varies in response to a variance of the resistance of the resistor unit.

6. The apparatus according to claim 1, wherein contamination of the filter is detected in real-time based on the calculated THD.

7. The apparatus according to claim 6, wherein the filter is contaminated when the calculated THD is greater than or equal to a predetermined THD.

8. The apparatus according to claim 7, further comprising an alarm that is activated when the filter is contaminated.

9. A method for detecting a filter contamination of a fuel cell, the method comprising:
   transmitting at least one signal;
   passing the transmitted at least one signal through a resistor unit including a silver compound having a resistance value which varies according to a chemical reaction and determining whether contamination by sulfur occurs when the resistance value falls;

receiving the at least one signal passing through the resistor unit, and determining the contamination of a filter using a total harmonic distortion (THD) calculated by dividing a harmonic size of a frequency output from the signal receiver by a harmonic size of a frequency input to the signal transmitter and multiplying the divided result by 100.

10. The method according to claim 9, further comprising passing the at least one signal through another resistor unit.

11. The method according to claim 9, wherein the resistor unit is formed in a thin film form including silver.

12. The method according to claim 9, wherein the resistor unit is formed in a hot film structure, a heat ray structure, or a semiconductor heater structure.

13. The method according to claim 9, wherein the received at least one signal has a frequency which varies in response to a variance of the resistance of the resistor unit.

14. The method according to claim 9, further comprising detecting contamination of the filter in real-time based on the calculated THD.

15. The method according to claim 14, wherein the filter is contaminated when the calculated THD is greater than or equal to a predetermined THD.

16. The method according to claim 15, further comprising activating an alarm when the filter is contaminated.

* * * * *